US010092181B2

(12) United States Patent
Yang et al.

(10) Patent No.: US 10,092,181 B2
(45) Date of Patent: Oct. 9, 2018

(54) METHOD OF IMAGING MULTIPLE RETINAL STRUCTURES

(71) Applicants: Qiang Yang, Rochester, NY (US); Ethan Andrew Rossi, Rochester, NY (US)

(72) Inventors: Qiang Yang, Rochester, NY (US); Ethan Andrew Rossi, Rochester, NY (US)

(73) Assignee: University of Rochester, Rochester, NY (US)

( * ) Notice: Subject to any disclaimer, the term of this patent is extended or adjusted under 35 U.S.C. 154(b) by 135 days.

(21) Appl. No.: 15/097,040

(22) Filed: Apr. 12, 2016

(65) Prior Publication Data

US 2016/0317031 A1 Nov. 3, 2016

Related U.S. Application Data

(60) Provisional application No. 62/154,435, filed on Apr. 29, 2015.

(51) Int. Cl.
*A61B 3/14* (2006.01)
*A61B 3/12* (2006.01)
(Continued)

(52) U.S. Cl.
CPC .............. *A61B 3/12* (2013.01); *A61B 3/0025* (2013.01); *A61B 3/0058* (2013.01);
(Continued)

(58) Field of Classification Search
CPC ...... A61B 3/0025; A61B 3/102; A61B 3/0041; A61B 3/1025; A61B 3/14; A61B 3/13; A61B 3/0008; A61B 3/0075; A61B 3/1015; A61B 3/12; A61B 3/1233; A61B 3/132; A61B 3/145; A61B 3/18; A61B 5/0064; A61B 5/0086; A61B 5/015; A61B 5/1077; A61B 5/411; G02B 2027/014; G02B 27/017; G02B 27/0172; G02B 27/2221; G02B 27/2264; G02B 26/026; G02B 27/2207; G02B 27/2228; G02B 27/0031; G02B 27/0068
(Continued)

(56) References Cited

U.S. PATENT DOCUMENTS 8,226,236 B2 7/2012 Williams et al.
9,254,083 B2 2/2016 Nozato et al.
(Continued)

OTHER PUBLICATIONS

Rossi et al.: "In vivo imaging of retinal pigment epithelium cells in age related macular degeneration" Biomedical Optics Express, 4(11), 2527-2539 (Oct. 18, 2013).
(Continued)

*Primary Examiner* — Brandi Thomas
(74) *Attorney, Agent, or Firm* — Andrew J. Anderson, Esq.; Harter Secrest & Emery LLP

(57) ABSTRACT

Methods and apparatus for imaging multiple retinal structures and montaging of multiple retinal images are provided. The method involves cross-correlating images from different imaging channels to compensate for intra-frame distortion due to retinal movement during image acquisition, and conducting a second cross-correlation to filter out any motion artifacts in the images. The resultant images are combined to generate a composite image. The method also involves controlling light directed on the retina spatially and temporally.

17 Claims, 4 Drawing Sheets

(51) Int. Cl.
  *A61B 3/00* (2006.01)
  *A61B 3/13* (2006.01)
  *G02B 27/00* (2006.01)
  *A61B 3/10* (2006.01)

(52) U.S. Cl.
  CPC .......... *A61B 3/1015* (2013.01); *A61B 3/1025* (2013.01); *A61B 3/13* (2013.01); *A61B 3/14* (2013.01); *G02B 27/0031* (2013.01); *G02B 27/0068* (2013.01)

(58) Field of Classification Search
  USPC ........ 351/200, 205, 206, 209–211, 221, 222, 351/243–246
  See application file for complete search history.

(56) References Cited

U.S. PATENT DOCUMENTS

| | | | | |
|---|---|---|---|---|
| 2012/0274902 | A1* | 11/2012 | Baranton | A61B 3/14 351/206 |
| 2015/0070655 | A1* | 3/2015 | Rossi | A61B 3/12 351/214 |

OTHER PUBLICATIONS

Yang et al.: "Closed-loop optical stabilization and digital image registration in adaptive optics scanning light ophthalmoscopy" —Biomedical Optics Express, 5(9), 3174-3191 (Aug. 26, 2014).

Morgan et al.: In Vivo Autofluorescence Imaging of the Human and Macaque Retinal Pigment Epithelial Cell Mosaic Invest. Ophthalmol. Vis. Sci. 50(3), 1350-1359 (2009).

Yang et al.: "Calibration-free sinusoidal rectification and uniform retinal irradiance in scanning light ophthalmoscopy" Opt Lett. Jan. 1, 2015; 40(1): 85-88.

Scoles et al.: "In vivo dark field imaging of the retinal pigment epithelium cell mosaic" Biomedical Optics Express vol. 4, No. 9, 1710-1723, Sep. 1, 2013.

Scoles et al.: "In Vivo Imaging of Human Cone Photoreceptor Inner Segments" Investigative Opthalmology & Visual Science, Jul. 2014 vol. 55 No. 7 4244-4251.

Chui, et al.: "The use of forward scatter to improve retinal vascular imaging with an adaptive optics scanning laser ophthalmoscope" Biomedical Optics Express, vol. 3, No. 10, 2537-2549, Oct. 1, 2012.

Rossi et al.: "Imaging retinal mosaics in the living eye;" Eye (2011) 25, 301-308, © 2011 Macmillan publishers Limited.

Pinhas et al.: "Assessment of Perfused Foveal Microvascular Density and Identification of Nonperfused Capillaries in Healthy and Vasculopathic Eyes;" Investigative Ophthalmology & Visual Science, Dec. 2014 vol. 55 No. 12 8056-8066.

Reimers et al.: Spectral Full-Field Displays for Spectrometers Classical Optics 2014; ITh3A.5.pdf; © 2014 OSA.

Xu et al.: "Design of freeform mirrors in Czerny-Turner spectrometers to suppress astigmatism" May 20, 2009 / vol. 48, No. 15 / Applied Optics 2871-2879.

* cited by examiner

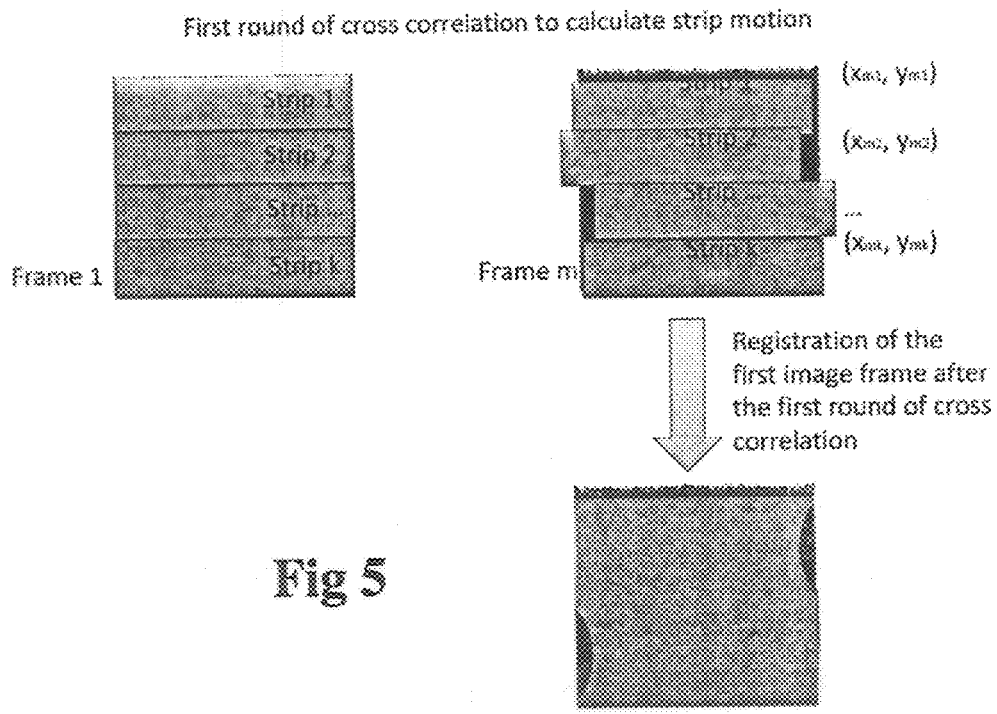
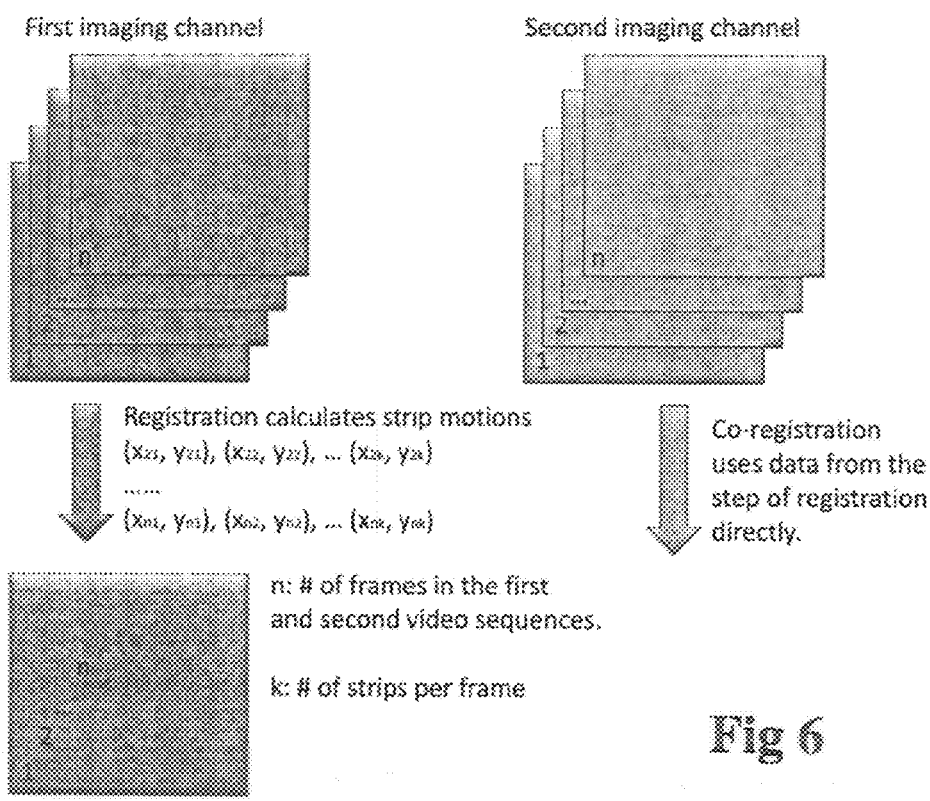

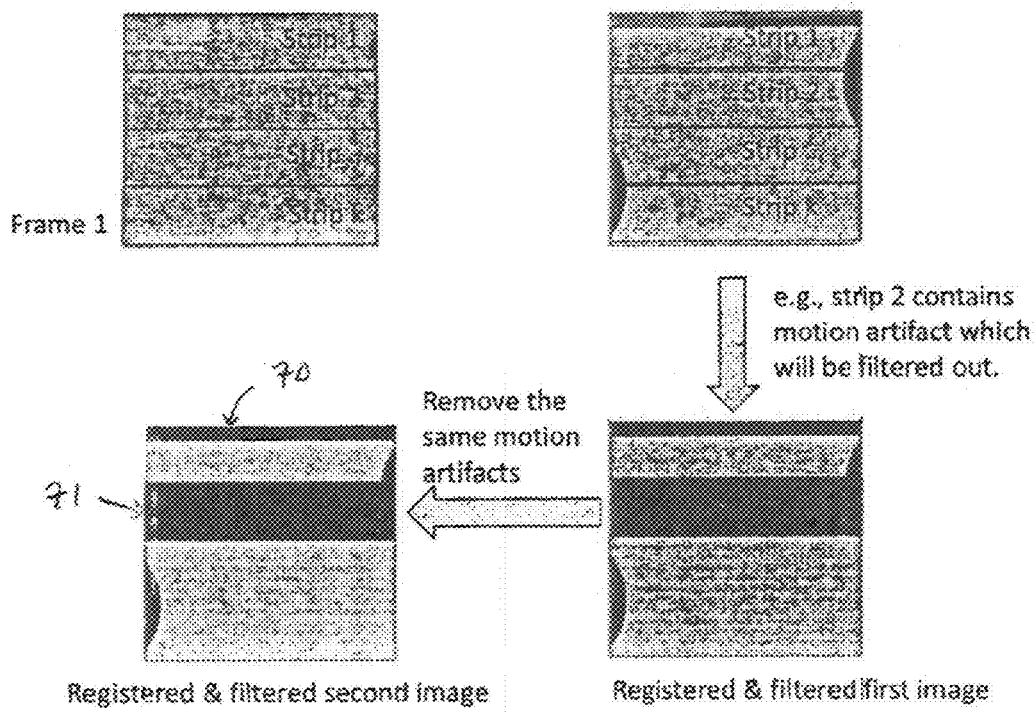

METHOD OF IMAGING MULTIPLE RETINAL STRUCTURES

STATEMENT REGARDING FEDERALLY SPONSORED RESEARCH OR DEVELOPMENT

This invention was made with Government support under Grant Nos. EY014375, and EY001319, awarded by the National Institutes of Health/National Eye Institute. The government has certain rights in the invention.

REFERENCE TO A "SEQUENCE LISTING"

Not applicable.

BACKGROUND OF THE INVENTION

Non-invasive imaging of various retinal structures, such as retinal pigment epithelial (RPE) cells, of the living eye is important, especially for studying, diagnosing and monitoring diseases of the living human eye. Confocal imaging systems, including those using adaptive optics, have been employed to obtain images of various retinal structures. For example, fluorescence adaptive optics scanning light ophthalmoscope (AOSLO) techniques have been used to image RPE cells in normal and diseased eyes. However, the prior approaches have involved relatively high light levels, focusing challenges and/or relatively long post-processing of image data, thus limiting clinical applications of these methods.

SUMMARY

This invention provides a method, and an apparatus, to permit routine and practical imaging of retinal structures and montaging of multiple images in a clinical setting. This invention provides imaging concurrently structures from multiple retinal layers.

The invention includes a method comprising:
 direct light on a portion of the retina to achieve irradiance;
 acquire a first image frame and register successive image frames of a portion of the retina from a first imaging channel, and simultaneously acquire and co-register second image frames of the portion of the retina from a second, different imaging channel;
 divide the first image frame and each successive image frame into corresponding multiple strips, and cross-correlate each successive image frame strip with a corresponding first image frame strip to compensate for intra-frame distortion due to retinal movement during image acquisition, and apply these strip motions to the second image frames and co-register the second image strips;
 re-divide the registered successive image frames into second strips, and conduct a second cross-correlation of each corresponding second strip, thereby filtering out any motion artifacts in the registered images and register such final first images, and
 combine the final first images and generate a composite image for the first imaging channel, and co-register and combine final second images and generate a composite image for the second imaging channel.

The method may further comprise simultaneously acquiring and co-registering third (and/or fourth or more) image frames of the portion of the retina from a third (and/or fourth or more), different imaging channel; applying strip motion from the first successive image frames to the third and/or fourth image strips based on the registered final first images, and combining final third and/or fourth images and generating a composite image for each individual imaging channel thereon.

The method may further comprise controlling timing and intensity of light directed on the portion of the retina, such that light exposure on said retina is minimized.

The method may further comprise monitoring timing and intensity of light directed on the portion of the retina, and discontinuing direction of light if a maximum value is reached.

Light may be directed with a light source including a shutter, and the method further comprising controlling the shutter so that light is directed on the portion of the retina only during acquisition of images thereof. The light source may include an acousto-optic modulator, and the method further comprising modulating the power of light directed on the portion of the retina, thereby achieving uniform retinal irradiance.

Images may be acquired and registered with a scanning light ophthalmoscope, such as an adaptive optics scanning light ophthalmoscope including a wavefront corrector.

In this method, the first channel wavelength and the second channel wavelength may be different or identical.

The irradiance may include at least one of fluorescence, reflectance and scattering.

The second correlation in this method may be initiated while additional second images are still being acquired, or the second correlation may be initiated after second images are acquired.

The composite images may be displayed on a display device in real-time. Additionally, this composite image may be a high signal-to-noise ratio image of structures from multiple retinal layers of a living animal. Images of structures from multiple retinal layers of a living animal may be obtained concurrently.

The method may further comprise comparing the cross-correlated first image strips with a threshold, and registering first image strips meeting the threshold. The threshold may include an amount of motion between the registered first image and a corresponding first imaging image being less than a single pixel, or greater than a single pixel.

This invention provides a method of imaging multiple structures of a retina comprising:
 direct light on a portion of the retina to achieve irradiance;
 acquire and register a first image frame of a portion of the retina from a first imaging channel, and simultaneously acquire and co-register second image frames of the portion of the retina from a second, different imaging channel;
 cross-correlate the first image frame and successive first image frames to filter out any motion artifacts in the registered first image frames, and register separately final, filtered first and second images, and
 combine the final first images and generate a composite image, and combine the final second images and generate a composite image,
 wherein light is controlled spatially and temporally.

This method may further comprise monitoring timing and intensity of light directed on the portion of the retina, and discontinuing direction of light if a maximum value is reached. The light may be directed with a light source including a shutter, and the method further comprising controlling the shutter so that light is directed on the portion of the retina only during acquisition of images thereof. The light source may include an acousto-optic modulator. The images may be acquired and registered with an adaptive optics scanning light ophthalmoscope including a wavefront corrector.

This invention provides an apparatus comprising:

a light source that directs light on a portion of the retina to achieve irradiance;

an image acquirer that acquires a first image frame from a first imaging channel and a second image frame from a second imaging channel of the portion of the retina;

a first correlation module that: divides a first image frame and successive first image frames into corresponding multiple strips, cross-correlates each successive first image frame strip with a corresponding first image frame strip to compensate for intra-frame distortion due to retinal movement during image acquisition; and co-registers second image strips from the first correlation;

a second correlation module that: divides the registered first image strips into second image strips, and conducts a second cross-correlation of each corresponding second image strip, thereby filtering out any motion artifacts in the registered images, and registers such final first images and co-registers final second images, combines the final first images and generates a composite image, and combines the final second images and generates a composite image; and a display that displays the composite images.

The light source may further comprise a shutter. The apparatus may further comprise a controller for the shutter so that light is directed on the retina only during acquisition of images thereof.

The light source may include an acousto-optic modulator.

The image acquirer may include a scanning light microscope or scanning light ophthalmoscope, including an adaptive optics scanning light ophthalmoscope including a wavefront corrector.

The composite image may be displayed on the display in real-time.

The displayed composite image may be a high signal-to-noise ratio image of structures from multiple retinal layers of a living animal.

The first and second modules may conduct the first and second cross-correlations while the image acquirer acquires additional images.

BRIEF DESCRIPTION OF THE DRAWINGS

FIGS. 4 to 6 schematically illustrate a first cross correlation of image frames.

FIG. 7 schematically illustrates a second cross correlation of image frames.

DETAILED DESCRIPTION

As discussed above, it has been shown that RPE cells can be imaged with fluorescence AOSLO in normal and diseased eyes. However, high light levels, focusing challenges, and/or long post-processing of data times have limited clinical application of these methods. In particular, the low signal of fluorescence images and the long post-processing time has previously prevented images from being immediately inspected during imaging to ensure that focus, etc., is set appropriately. This invention addresses these problems that hinder routine imaging of the retinal structures in a clinical setting.

According to some aspects of this invention, the efficiency of image acquisition and processing is improved, thereby improving the quality of the final composite images while achieving real-time viewing of such final images. A first cross-correlation of images compensates for intra-frame distortion of image frames due to retinal movement during image acquisition. A second cross-correlation of images filters out remaining motion artifacts. Thus, the quality of images for combining to obtain a composite image is improved. For example, the composite image is a high-signal-to-noise ratio image. Additionally, the cross-correlations may be run in real-time. In clinical applications, therefore, real-time viewing of high quality composite images is possible.

According to some aspects of this invention, retinal structures may be imaged more efficiently by precisely controlling light directed on the retina, thereby limiting retinal exposure to light. The light may be controlled spatially and temporally. By controlling light spatially, a longer total imaging time at the reduced exposure level, is provided, thereby increasing the amount of imaging time. By controlling the light temporally, e.g., using light only when necessary to acquire images, a longer total imaging time is again provided. The longer imaging time allows for the acquisition of more images for combining to generate a composite image. In addition, the acquisition of more images makes it possible to montage images—i.e., acquire overlapping images from adjacent retinal areas and "stitch" them together.

As one example for clinical applications, the montaging of adjacent, overlapping retinal areas permits imaging of multiple retina structures. As another example, such montaging permits one to view an essentially contiguous mosaic of RPE cells in normal eyes, or to observe disruptions in this mosaic in diseased eyes.

Accordingly, this invention permits real-time viewing of retinal structures on a microscopic scale and of high resolution across relatively large retinal areas in the living eye.

Figure 1:
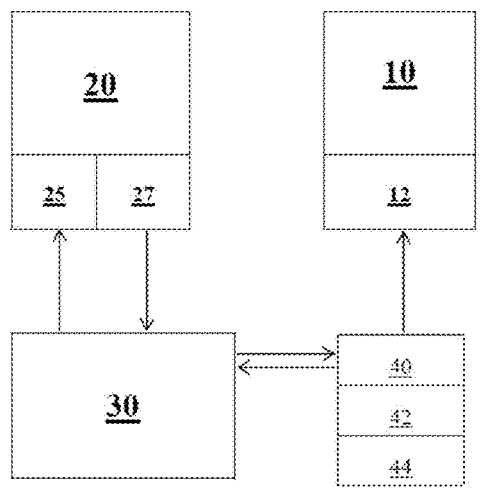
FIGS. 1 and 2 schematically illustrate an imaging system.
Figure 2:
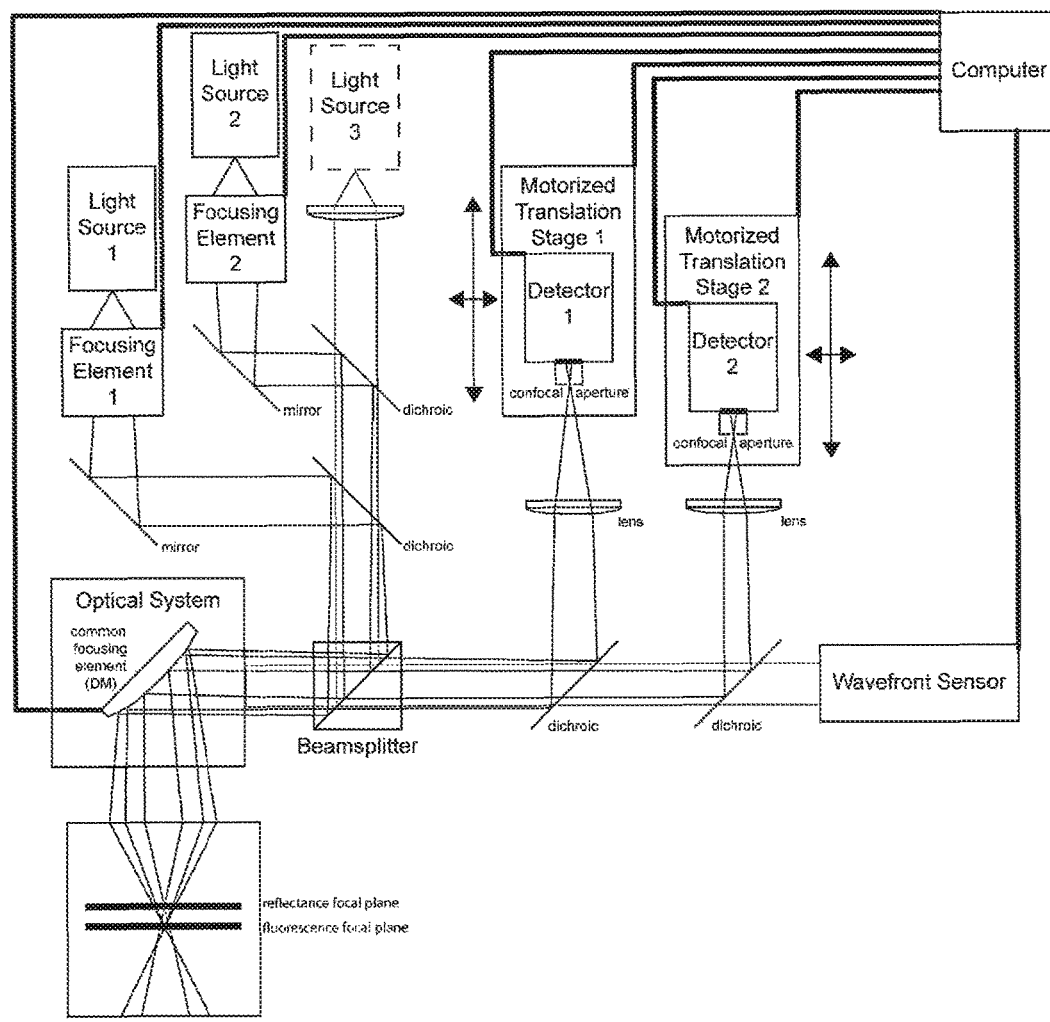

Aspects of the invention will be described with reference to the accompanying figures. FIGS. 1 and 2 schematically illustrate a representative imaging system, although this invention is applicable to other specific systems.

The system of FIG. 1 includes light source 10 and image acquirer 20. Light source 10 directs light on a portion of the retina to achieve irradiance. The irradiance may include at least one of fluorescence, reflectance and scattering, depending on the wavelength of light and the system used. Image acquirer 20 detects the irradiance from the portion of the retina.

Examples of the image acquirer include a scanning light ophthalmoscope. In the illustrated embodiment, image acquirer 20 includes an adaptive optics scanning light ophthalmoscope (AOSLO) including a wavefront corrector, such as a deformable mirror. The AOSLO will generally include adaptive optics closed-loop control and have an interface 25 to accept focus commands for the deformable mirror. Image acquirer 20 will generally include an imaging aperture, such as a confocal imaging aperture, for each wavelength of light.

Module 30 controls focusing of the deformable mirror and focus of the confocal imaging apertures. Module 30 sends deformable mirror focus commands to the interface of image acquirer 20 which adjusts the deformable mirror focus in the common optical path. Also, it sends commands to module 40 for returning mean pixel values (MPV) of images from multiple wavelengths. These MPVs are associated with deformable mirror focus and confocal imaging aperture positions. From the MPVs, module 30 runs an iterative Nelder-Mead simplex algorithm to adjust confocal imaging aperture positions of the detectors for light of the various wavelengths in three dimensional space. In this regard, module 30 sends commands to interface 27 which adjusts the position of the confocal image apertures, for example, mounted on a motorized stage. Module 30 plots the relationship between MPV and deformable mirror focus and finds the best foci for each different wavelength.

Various known methods may be employed to position the confocal imaging aperture. Additionally, a method of automatically positioning the confocal aperture in the confocal position is described in U.S. application Ser. No. 14/482,195, filed Sep. 10, 2014 and entitled "Apparatus and Method for Automatic Alignment in an Optical System and Applications", the disclosure of which is incorporated by reference in its entirety.

Module 40 performs several functions, also. Based on commands from module 30, it determines when to open shutter 12 of light source 10 to permit light to be directed on the retina and when to shut the shutter 12. Essentially, visual light directed on the retina is strictly controlled, so as to avoid any unnecessary light exposure. As an example, visible light can be harmful to the retina, and clinical applications involving imaging of the human retina must ensure that the retina is not overexposed to visible light.

One manner of strictly controlling light exposure is to employ an electromechanical or electronic shutter for shutter 12. The shutter 12 is opened under two conditions: (1) when there is a request of MVP from module 30; and (2) when module 40 is recording images.

To further ensure safety, a maximum light exposure for each individual imaging area may be preset in software of Module 40, based upon power of the light source and the desired safety limits, whereby the software dynamically calculates total light exposure. The remaining exposure time, i.e., the time remaining before the predetermined safety threshold is met, may be displayed for the user. If the safety threshold of maximum light exposure is reached, module 40 directs permanent closing of shutter 12, unless such safety flags are cleared manually, for example, for imaging a different subject on the system.

Another manner of strictly controlling light exposure on the retina is to employ a fast optical shutter for shutter 12, such as an acousto-optic modulator (AOM). An AOM can switch between on and off positions in the range of tens to hundreds of nanoseconds, and thus, is much faster than the electromechanical shutter. Additionally, an AOM can modulate light power sufficiently fast to achieve uniform irradiance of the portion of the retina being imaged in a fast scanning system.

Figure 3:
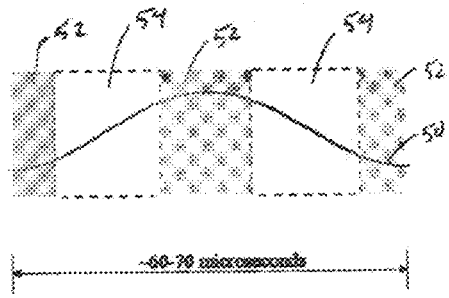
FIG. 3 schematically illustrates power modulation of an acousto-optic modulator employed for light control.

FIG. 3 illustrates power modulation of an AOM employed as shutter 12. The sinusoidal curve 50 illustrates motion of the resonant scanner in an illustrative AOSLO with a frequency of approximately 13-16 kHz. Hence, the period cycle is approximately 60-70 microseconds. In such an illustrative imaging system, data from the slower motion areas of the resonant scanner, corresponding to the shaded areas 52 of FIG. 3, is usually discarded since it often contains severe image distortion. Therefore, only data in the two dashed areas 54 of FIG. 3 is used. In other words, the dashed areas may be defined as an "imaging window" while the full sinusoidal cycle of scanner motion may be defined as a "scanning window". A fast AOM has the capability to turn off light during the shaded area of the cycle, and with proper modulation, achieve uniform retinal irradiance.

Accordingly, module 40, in conjunction with shutter 12, may control light directed on the portion of the retina spatially and temporally.

Module 40 includes modules 42 and 44. Generally, module 42 performs a first cross-correlation to compensate for intra-frame distortion of image frames due to retinal movement during image acquisition. Generally, module 44 performs a second cross-correlation to filter out any remaining motion artifacts in the image frames.

After achieving irradiance on the position of the retina being imaged, a first image frame of the portion of the retina is acquired and registered from a first imaging channel. Simultaneously second image frames of the portion of the retina are acquired and co-registered from a second, different imaging channel.

As one example, the first imaging channel may be near-infrared wavelength, to obtain a reflectance image of the retinal portion, and the second imaging channel may be visible light used in conjunction with intrinsic or extrinsic fluorophores, to obtain fluorescent images. However, images from visible light backscattered from the retina may be obtained, also. Further, the first and second imaging channels may employ light of the same wavelength, provided separate detectors and beam-splitting is employed.

In any event, because of eye motion, any given single frame usually has an appreciable amount of intra-frame distortion. Accordingly, in the first correlation, the first image frame is divided into multiple strips, and each successive first image frame is divided into corresponding multiple strips. Each successive first image frame strip is correlated with the corresponding first image frame strip to compensate for any intra-frame distortion of the first image frames due to retinal movement during image acquisition. The resultant first image strips are registered. The resultant second image strips are co-registered based on the correlation of the first images.

Figure 4:
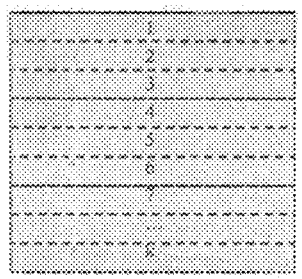
Figure 4:
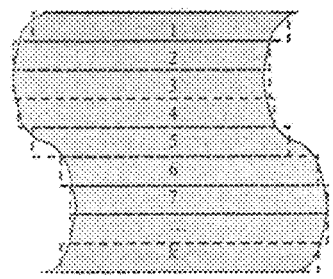

This is schematically illustrated in FIG. 4, where first image frame A has been divided into multiple strips 1 to k, and a successive first image frame B has been divided into corresponding multiple strips 1 to k. Motion from each strip pair between A and B is then calculated. A method employing co-registration of fluorescent images to adjust for eye motion during image capture is described in U.S. Pat No. 8,226,236 (Williams et al.), the disclosure of which is incorporated by reference in its entirety.

FIGS. 5 and 6 illustrate further this first correlation.

When such cross-correlation calculates motion between the corresponding strip pairs (e.g., in FIG. 4, A and B1, A2 and B2, etc.), the accuracy of the result is often highly dependent on image quality from the relevant strip pair. For example, ambiguity may appear on the result of the cross-correlation when one of the strips, or both of the strips, have minimal image features or if noise dominates. One approach to addressing this is to set a fixed threshold for the reliability of the correlation coefficient. However, the setup of this threshold is somewhat arbitrary because the correlation coefficient between two strips is not only dependent on the image quality, but also on the relative motion. As a consequence, incorrect motions from cross-correlation sometimes will be treated as correct ones, and therefore, they appear on the registered images as motion artifacts. Although one can discard the whole registered images containing motion artifacts, in doing so, one is discarding useful data, as the other portion of images contain useful data.

To resolve this issue, this invention employs the second cross-correlation of module 44. The second cross-correlation involves re-dividing the registered first image strips into second strips, and conducting a second cross-correlation of each corresponding second strip, thereby filtering out any motion artifacts in the first registered images. The final, filtered first images are registered, and the final, filtered second images are registered separately. FIG. 7 illustrates this second cross correlation.

Due to the fact that the amount of motion sub-pixel from any strip pair between the first image frame and the registered first images, strip size for the second round of cross-correlation can be as small as possible as long as the strips contain sufficient data and image features. Potentially, the size of a strip can be reduced to a single line. Smaller strip size offers two advantages: (1) it reduces computational time, and (2) it discards only motion artifacts and keeps all remaining useful data for eventual combining into a final composite image. FIG. 7 illustrates the result of the registered second image 70 after the second round of cross-correlation where the motion artifact 71 has been filtered out. This image contains true registered image features which may be combined with other registered and filtered images. In other words, the motion artifact has been filtered out, and the remaining image containing "true" features, and useful data, is used for combining with other registered and filtered images.

In order to filter out the motion artifacts in real time, the second cross-correlation may be implemented by different approaches: (1) at the end of the current frame during the retrace period of the slow scanner, where the retracing time is adjustable based on computational time of the cross-correlation; or (2) immediately after detection of strip motion from the first round of cross-correlation, which is used to drive a tracking mirror to track eye location. In approach (2), it is generally required for the algorithm to finish all the computation before the next strip is received. Also, in approach (2), the first cross-correlation calculates motion of the most recent strip, and the second cross-correlation processes registered images from the previous frame.

In an imaging system providing data from multiple wavelengths, i.e., systems where image frames of a portion of the retina are obtained from a third, different imaging channel (or more imaging channels), high-fidelity, filtered, final images from the second cross-correlation may be used to co-register and co-average images from these additional, other wavelength channels.

To run the second round of cross-correlation as efficiently as possible and to retain as much data of the combined images as possible, module 44 may include a dedicated processor to run the second cross-correlation in the background of the processor running the first cross-correlation in module 42, so that the computation of module 44 will be completely isolated from the computation of module 42 performing real-time eye tracking and digital registration.

The resultant final images are ultimately combined in known manners, such as averaging, integrating, subtracting, adding, and/or dividing the images. The combined final first images are used to generate a final composite image from the first imaging channel. The combined final second images are used to generate a final composite image from the second imaging channel.

It will be appreciated that the final composite images from the second imaging channel may be further combined with one another. For example, several composite images from the second imaging channel, generated from co-registration separated by short temporal intervals, may be registered and combined. This may be useful for compensating for temporal variation in the lateral position offset between images in the first imaging channel and images in the second imaging channel. Such variability may occur in the living eye, for example, from changes in transverse chromatic aberration (TCA) between the first and second imaging channel wavelengths caused by pupil movement from eye motion.

In cases where there is lateral position offset between the first and second channel images, such as may occur from TCA, this offset may be recovered by tracking the position of the pupil. A pupil camera may be triggered by the image acquirer to concurrently record real- time position of the pupil image. The amount of TCA is then calculated from the temporal sequence of the pupil image which has been synchronized with the recorded first and second images. This amount of TCA is then used to dynamically adjust co-registration of the second images in real time or in post processing.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A method of imaging multiple retinal structures comprising:
   direct light on a portion of the retina to achieve irradiance;
   acquire a first image frame and register successive image frames of a portion of the retina from a first imaging channel, and simultaneously acquire and co-register second image frames of the portion of the retina from a second, different imaging channel;
   divide the first image frame and each successive image frame into corresponding multiple strips, and cross-correlate each successive image frame strip with a corresponding first image frame strip to compensate for intra-frame distortion due to retinal movement during image acquisition, and apply these strip motions to the second image frames and co-register the second image strips;
   re-divide the registered successive image frames into second strips, and conduct a second cross-correlation of each corresponding second strip, thereby filtering out any motion artifacts in the registered images and register the first images, and
   combine the final first images and generate a composite image for the first imaging channel, and co-register and combine final second images and generate a composite image for the second imaging channel.

2. The method of claim 1, further comprising simultaneously acquiring and co-registering third image frames of a portion of the retina from a third, different imaging channel; and combining final third images and generating a composite image thereon.

3. The method of claim 1, further comprising controlling timing and intensity of light directed on the portion of the retina, such that light exposure on said portion is minimized.

4. The method of claim 1, wherein the light is directed with a light source including a shutter, and the method further comprises controlling the shutter so that light is directed on the portion of the retina only during acquisition of images thereof.

5. The method of claim 1, wherein the light source includes an acousto-optic modulator, and the method further comprises modulating the power of light directed on the portion of the retina, thereby achieving uniform retinal irradiance.

6. The method of claim 1, wherein images are acquired and registered with a scanning light microscope or scanning light ophthalmoscope.

7. The method of claim 6, wherein images are acquired and registered with an adaptive optics scanning light ophthalmoscope including a wavefront corrector.

8. The method of claim 1, wherein the first channel wavelength and the second channel wavelength are different.

9. The method of claim 1, wherein the irradiance includes at least one of fluorescence, reflectance and scattering.

10. The method of claim 1, wherein the second correlation is initiated while additional second images are still being acquired.

11. The method of claim 1, wherein the second correlation is initiated after second images are acquired.

12. The method of claim 1, wherein the composite images are displayed on a display device in real-time.

13. The method of claim 1, wherein the composite image is a high signal-to-noise ratio image of structures from multiple retinal layers of a living animal.

14. The method of claim 1, wherein the images of structures from multiple retinal layers of a living animal are obtained concurrently.

15. The method of claim 1, further comprising comparing the cross-correlated first image strips with a threshold, and registering first image strips meeting the threshold.

16. The method of claim 1, wherein several second final composite images generated from co-registration separated by short temporal intervals are registered and combined to compensate for temporal variation in a lateral position offset between the first imaging channel and second imaging channel.

17. The method of claim 1, wherein a lateral position offset between images of the first and second imaging channels is recovered by tracking pupil position.

* * * * *